United States Patent

Kelly et al.

[11] Patent Number: 6,066,093
[45] Date of Patent: *May 23, 2000

[54] DISPOSABLE ELECTRODELESS ELECTRO-DERMAL DEVICES

[75] Inventors: Robert J. Kelly, Camarillo, Calif.; William K. Wenger, Weehawken, N.J.; Thomas G. Lavine, Woodland Hills, Calif.

[73] Assignee: Unilead International Inc., Orinda, Calif.

[*] Notice: This patent is subject to a terminal disclaimer.

[21] Appl. No.: 08/783,912

[22] Filed: Jan. 16, 1997

Related U.S. Application Data

[63] Continuation-in-part of application No. 08/508,928, Jul. 28, 1995, abandoned.

[51] Int. Cl.$^7$ ............................................. A61B 5/0402
[52] U.S. Cl. ........................... 600/386; 600/391; 600/393
[58] Field of Search .................... 600/372, 383, 600/386, 388, 389, 390, 391, 392, 393

[56] References Cited

U.S. PATENT DOCUMENTS

| | | | |
|---|---|---|---|
| D. 313,652 | 1/1991 | Lavine | D24/17 |
| 3,910,260 | 10/1975 | Sarnoff et al. | 128/2.06 R |
| 4,102,331 | 7/1978 | Grayzel et al. | 128/2.1 E |
| 4,328,814 | 5/1982 | Arkans | 128/640 |
| 4,353,372 | 10/1982 | Ayer | 128/640 |
| 4,522,211 | 6/1985 | Bare et al. | 600/391 |
| 4,583,549 | 4/1986 | Manoli | 600/393 |
| 4,608,987 | 9/1986 | Mills | 128/639 |
| 4,674,511 | 6/1987 | Cartmell | 128/640 |
| 4,763,660 | 8/1988 | Kroll et al. | 600/393 |
| 4,957,109 | 9/1990 | Groeger et al. | 600/393 |
| 5,042,481 | 8/1991 | Suzuki et al. | 128/639 |
| 5,058,589 | 10/1991 | Ding et al. | 128/640 |
| 5,184,620 | 2/1993 | Cudahy et al. | 128/639 |
| 5,191,886 | 3/1993 | Paeth et al. | 600/393 |
| 5,224,479 | 7/1993 | Sekine | 128/644 |
| 5,257,631 | 11/1993 | Wilk | 128/710 |
| 5,307,818 | 5/1994 | Segalowitz | 128/696 |
| 5,327,888 | 7/1994 | Imran | 600/393 |
| 5,341,806 | 8/1994 | Gadsby et al. | 128/640 |
| 5,370,116 | 12/1994 | Rollman et al. | 128/644 |
| 5,465,727 | 11/1995 | Reinhold, Jr. | 128/710 |
| 5,507,290 | 4/1996 | Kelly et al. | 128/640 |
| 5,546,950 | 8/1996 | Shoeckert et al. | 128/696 |
| 5,678,545 | 10/1997 | Stratbucker | 128/640 |

FOREIGN PATENT DOCUMENTS

| | | |
|---|---|---|
| 122258 | 6/1972 | Denmark . |
| 0275811 | 7/1988 | European Pat. Off. . |
| 2619300 | 2/1989 | France . |

*Primary Examiner*—Lee Cohen
*Attorney, Agent, or Firm*—Fitzpatrick, Cella, Harper & Scinto

[57] ABSTRACT

A disposable electrodeless electro-dermal connector device includes a flexible non-conductive sheet having a fixed array of electrical conductor strips affixed thereon and positioned in a specific size configuration appropriate for electrocardiographic recording. The connector strips have a receptor pad end adapted for electrical connection with the skin for receiving electrical impulses and a terminal connection end which is adapted for connection with an electrocardiological measuring apparatus. Receptor pads $V_1$ and $V_2$ are attached approximately over the sternum at the fourth intercostal space and receptor pads $V_3$ and $V_4$ are attached over the ribs, with the distance between $V_1$ and $V_2$ being 2.00 inches ±0.56 inches, the distance between $V_2$ and $V_4$ being 3.5 inches ±1.00 inch.

33 Claims, 5 Drawing Sheets

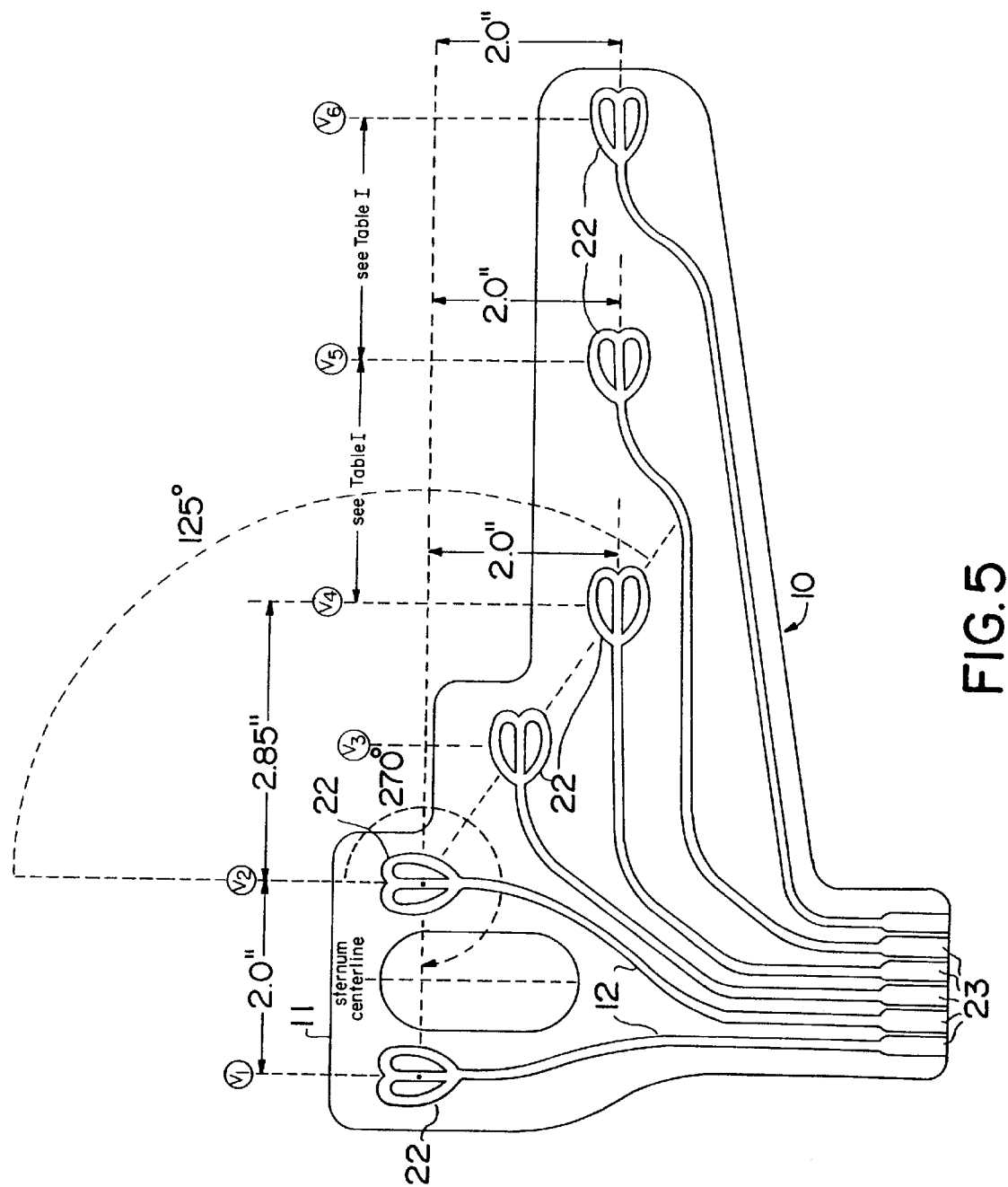

DISPOSABLE ELECTRODELESS ELECTRO-DERMAL DEVICES

RELATED U.S. APPLICATION

This application is a continuation-in-part of U.S. application Ser. No. 08/508,928, filed Jul. 28, 1995, now abandoned.

BACKGROUND OF THE INVENTION

1. Field of the Invention

This invention relates to a disposable medical device employing electrical signals to monitor or stimulate various parts of the body. More particularly, the present invention involves a device for establishing electrical connection to a patient's skin containing a fixed array of conductive paths of substantially the same electrical resistance for use with an electrocardiological measuring apparatus.

2. Description of the Prior Art

Prior art medical electrodes generally are combination structures including a metallic or otherwise conductive support member to which an electric wire from an assorted apparatus may be attached. Generally, electrocardiograms sometimes referred to as an EKG or ECG have ten cable leads which attach to various points on the upper and mid-torso of a patient to measure and analyze cardiac data.

Of primary concern when preparing for an electrocardiogram is accurate placement of the electrodes. The person responsible for attaching the electrodes and lead wires ("leads") of the EKG often has problems in attaching these multiple leads to the patient because the lead wires may tangle with one another or, in the case of suction-type electrodes, may become detached before or after they are all connected. Accurately placing and securing a large number of leads can be difficult and time consuming and requires the knowledge of a skilled technician or physician.

Periodic electrocardiograms can provide a cardiographic profile of a patient for early detection and diagnosis of cardiovascular diseases. For purposes of providing an accurate profile, it is important not only that the electrocardiogram be taken with sensors affixed accurately, but that the sensors are placed at the same location on the patient as for the previous electrocardiograms. The accuracy of the reproducible results is critical so that a series of electrocardiograms can be compared, between testing episodes, to provide a continuing profile of a patient for diagnosis and treatment of heart disease.

A full screen, ten electrode (twelve lead) electrocardiograph provides the most accurate picture for recognizing ischemic electrocardiographic changes. However, in urgent situations, including those electrocardiograms taken during an acute symptomatic episode of a cardiac patient, only two to four electrodes may be attached to the patient. Therefore, it would be advantageous and desirable to have a device which enables more leads to be accurately placed and quickly secured during an acute symptomatic episode.

On the other hand it may be necessary to quickly remove certain or all of the chest leads of the EKG when a patient is experiencing another heart attack in order to administer CPR, to massage the heart, administer drugs or apply electrical defibrillation paddles. Accordingly, valuable seconds are often lost in removing the chest leads of the EKG device in order to administer aid to the patient.

U.S. Pat. No. 4,328,814 to Arkans teaches a plurality of electrodes arranged in a strip. Each electrode has a conductive lead which runs to a single junction connector having one cable leading to the EKG device. This device is designed for an adult patient so that patients having larger or smaller torsos will have difficulty in using the device because the electrodes cannot be easily adjusted to accommodate a smaller or larger torso.

U.S. Pat. No. 4,353,372 to Ager discloses a plurality of electrodes which plug into a junction box connected to an EKG machine. Each of the electrodes includes wires molded into a central cable system which joins the junction box. This device does not include means for quickly attaching or removing the electrodes. For example, in an emergency situation if the electrodes must be removed quickly, the junction box must be disconnected first and then each of the electrodes must be detached. Although each electrode has a wire lead from the main molded cable, which may permit some adjustment in the placement of the electrodes on the upper portion of a human torso, the device is not entirely adequate for large adults or very small children because of the limited adjustment of each electrode.

U.S. Pat. No. 3,910,260 describes telephonic units for transmitting EKG signals to ECG receiving equipment which could be at a hospital or a physician's office. The transmission may take place in emergency vehicles where prior medical history may not be readily available. In order to obtain meaningful and reliable data ECG signals are necessary for the care providers.

U.S. Pat. No. 4,608,987 to Mills relates to a vest-like garment having a plurality of apertures adapted for receiving associated electrodes. However, the vest is not tailored for a specific patient and proper fit is provided by adjustable straps which may be secured by VELCRO material. Therefore, there is no assurance that the electrodes are placed at the same anatomical location upon reuse with the same patient.

U.S. Pat. No. 4,583,549 to Manoli relates to an ECG electrode pad having a flexible non-conductive pad provided with a plurality of electrodes. In this patent, the electrodes are positioned at various anatomically defined positions on the chest wall. Although different size pads are contemplated, this patent lacks any teaching or suggestion of how the sizes are dimensioned, how they would be determined, or even how a patient would be fitted with the proper size.

U.S. Pat. No. 5,184,620 to Cudahy discloses a multiple electrode pad for monitoring a patient's cardiac electrical activity. A flexible pad is equipped with a plurality of groups of electrodes. In one embodiment each group has two electrodes, and in another embodiment three electrodes form each group.

U.S. Pat. No. 5,224,479 to Sekine illustrates a vest-like ECG diagnostic pad provided with upper limb lead electrodes, precordial lead electrodes and flank lead electrodes. The precordial lead electrodes are positioned on the pad to come into contact with anatomically prescribed locations on the midriff portion of the patient.

U.S. Pat. No. 5,507,290 to Kelly relates to an electrodeless EKG sensor sheet provided with electrical conducting strips or wires. The sensor sheet is made of a flexible, non-conductive substrate and can include means for positioning the sheet on the chest of a patient. The electrical conducting strips are set in a predetermined pattern on the sensor sheet. The patent does not relate to providing different size sensor sheets.

None of the prior art devices disclose a low cost solution for obtaining repeatable placement of sensors for accurate and readable ECG signals in the field by unskilled individuals.

Because of the inadequacies of prior art devices there is a need for a system which prevents EKG electrode leads from being entangled; provides quick removal of some of the electrodes while leaving the remaining electrodes in position when it is necessary to administer aid to a patient having a heart attack; provides accurate repeatable placement of electrodes at substantially the same anatomical location; accurately and repeatedly obtains signals from body electrodes by efficient and effective electrical transmission; may be attached by unskilled persons; and may be available in various sizes to accommodate different size patients.

SUMMARY OF THE INVENTION

The present invention, in one aspect involves a disposable non-conducting flexible sheet incorporating a fixed array of electrical conducting strips emanating from a terminus that can connect to a standard electrocardiographic cable or telemetric unit. The strips are used as both collectors and as transmitters for electrical impulses. Conventional sensory electrodes are unnecessary since the device can function without them. More particularly, the invention relates to a disposable, electro-dermal connector device comprising a flexible non-conductive sheet comprising a fixed array of electrical conductor strips affixed thereto having a receptor pad end and a terminal connection end. The array is positioned in a configuration used for electrocardial recording, whereby the flexibility of the connector and adhesion of the surface of the flexible sheet to skin are substantially enhanced.

Each strip includes a first end portion or receptor end adapted for electrical connection with the skin for receiving electrical impulses. A second end portion terminates in a common electrical connection or cable junction which is adapted for connection with a standard type of cable junction for connection with the electrocardiograph device.

The conductive strips may be printed on the single layer non-conductive film or sheet by any conventional printing or silk screening type of process. The portion of the strip which need not be exposed can be coated or covered with a non-conductive (dielectric) coating. Conductor strips which are less than 20 micrometers in thickness provide enhanced flexibility without distorting the electrical signal.

More particularly, this aspect of the invention relates to a disposable electrodeless electro-dermal connector device comprising a flexible non-conductive sheet comprising a fixed array of electrical conductor strips affixed thereon and positioned in a specific size configuration for standard electrocardiographic recording. The conductor strips have a receptor pad end adapted for electrical connection with the skin for receiving electrical impulses and a terminal connection end which is adapted for connection with an electrocardiological measuring apparatus. Receptor pads $V_1$ and $V_2$ are attached approximately on either side of the sternum at the fourth intercostal space and receptor pad $V_3$ is positioned midway between $V_2$ and $V_4$. $V_5$ is equidistant between $V_4$ and $V_6$. The distance between $V_1$ and $V_2$ is about 2.00 inches ±0.56 inches, i.e., $V_1$ is 1.00 inch ±0.28 inches to the right and $V_2$ is 1.00 inch ±0.28 inches to the left, measured equidistantly from the centerline of the sternum. The distance between V2 and $V_4$ is about 3.5 inches ±1.00 inch, and $V_3$ is located substantially midway between $V_2$ and $V_4$.

In another aspect of the invention, the flexible non-conductive sheet is provided in a plurality of sizes, with each size having receptor ends $V_1$, $V_2$, $V_3$ and $V_4$ at substantially the same locations and having receptor ends $V_5$ and $V_6$ at different locations depending on size. In this regard, the locations of the receptor ends $V_5$ and $V_6$ are based on a measured distance between a midclavicular line and a midaxillary line on the chest of the patient.

In still another aspect of the invention, a method of sizing a patient for fitting an electrodeless electro-dermal connector device is disclosed. The flexible non-conductive sheet comprises a fixed array of electrical conductor strips affixed thereon and positioned in a specific size configuration appropriate for standard electrocardiographic recording, the conductor strips having receptor ends $V_1$ to $V_6$ adapted for electrical connection with the skin for receiving and transmitting electrical impulses and a terminal connection end which is adapted for connection with an electrocardiological measuring apparatus, wherein the distance between $V_1$ and $V_2$ is 2.00 inches ±0.56 inches, and the distance between $V_2$ and $V_4$ is about 3.5 inches +1.00 inch, with $V_3$ located substantially midway between $V_2$ and $V_4$ and $V_5$ is generally equidistant between $V_4$ and $V_6$. The method comprises the steps of measuring the distance between a midclavicular line and a midaxillary line on the chest of the patient, and selecting a connector device based on the measured distance.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 5 illustrates the positioning of a dimensional array according to this invention.

DESCRIPTION OF THE PREFERRED EMBODIMENTS

Figure 1:
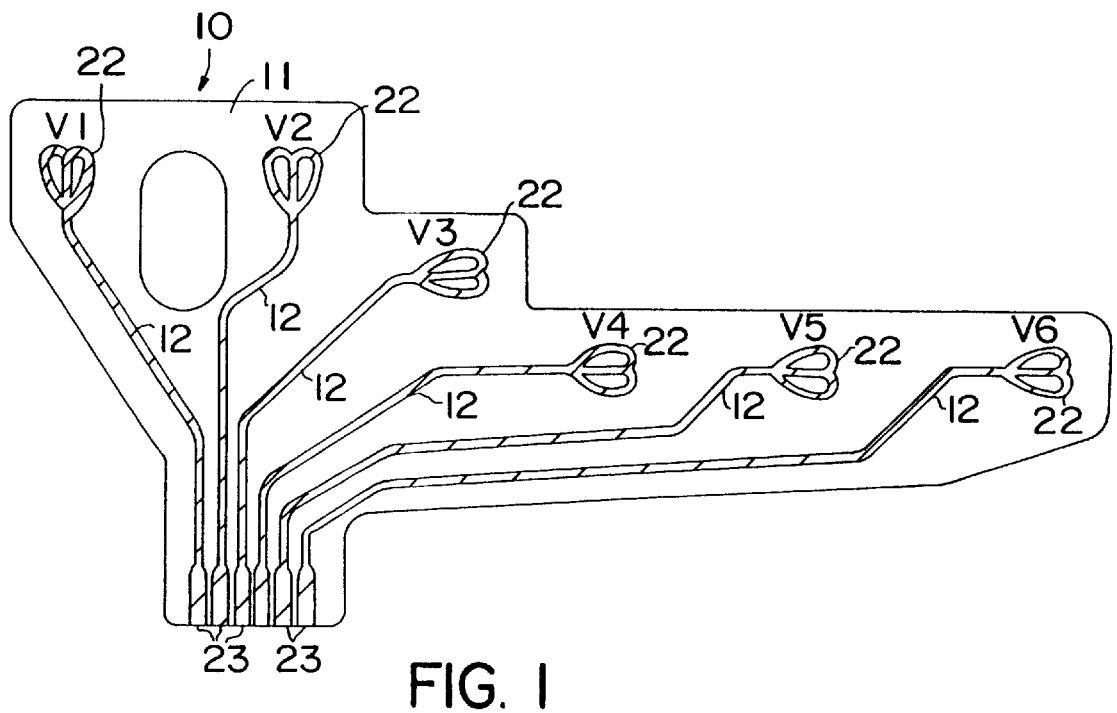
FIG. 1 shows a preferred device of the present invention provided with electrode end sensors for attachment to the torso of a patient.

Referring now to the drawings, FIGS. 1 and 5 illustrate an electro-dermal connector device 10 in accordance with the present invention. In this embodiment, an array of electrodeless receptors 22 are positioned at a predetermined dimensional array $V_1$–$V_6$ on the device 10.

FIG. 1 illustrates the connector device of the present invention for placement on the chest of a patient. The connector device is formed of a flexible non-conducting sheet 11 incorporating multiple conductor strips 12 for connection to a standard electrocardiographic receiving unit. The conductor strips 12 have at their first end sensors or receptors 22 which are positioned on the sheet and spaced relative to each other, whereby the receptors 22 are positioned in a specific size configuration appropriate for electrocardial recordings.

Each strip 12 includes at its second end a terminal conductor end 23 to engage a common electrical connection or cable junction (not shown) for connection with the electrocardiograph device (not shown).

When in use, an electrically conductive ink containing a biocompatable adhesive gel is applied to the body contacting side of sheet 11 at each receptor 22 of connector 12 for adhesion to the skin of the patient for providing electrical connection between each of the precordial ends and the terminal end 23 connected to the proper receiving devices (not shown).

The adhesive gel coated area of the connector device includes at least one release liner in releasable adhesive contact with the gel. Each of the conductor strips 12 are less than 10, and preferably less than 5, micrometers in thickness whereby the flexibility of the connector and adhesion of the gel surface to the skin are substantially enhanced.

FIG. 1 shows the connector array ($V_1$, $V_2$, $V_3$, $V_4$, $V_5$ and V6) on flexible sheet 11 which is designed to adhere to a human torso so that the receptors 22 are located below the sternum, over the epigastric region of the abdomen and near the centerline of the torso. The flexible sheet 11 can be substantially transparent and includes an opening in the proximate center which is intended to span the upper portion of the sternum of the patient. The sheet may include indicia adjacent to or on each of the conductor strips to facilitate correct placement of the receptors on the precordial areas of the human torso.

Figure 2:
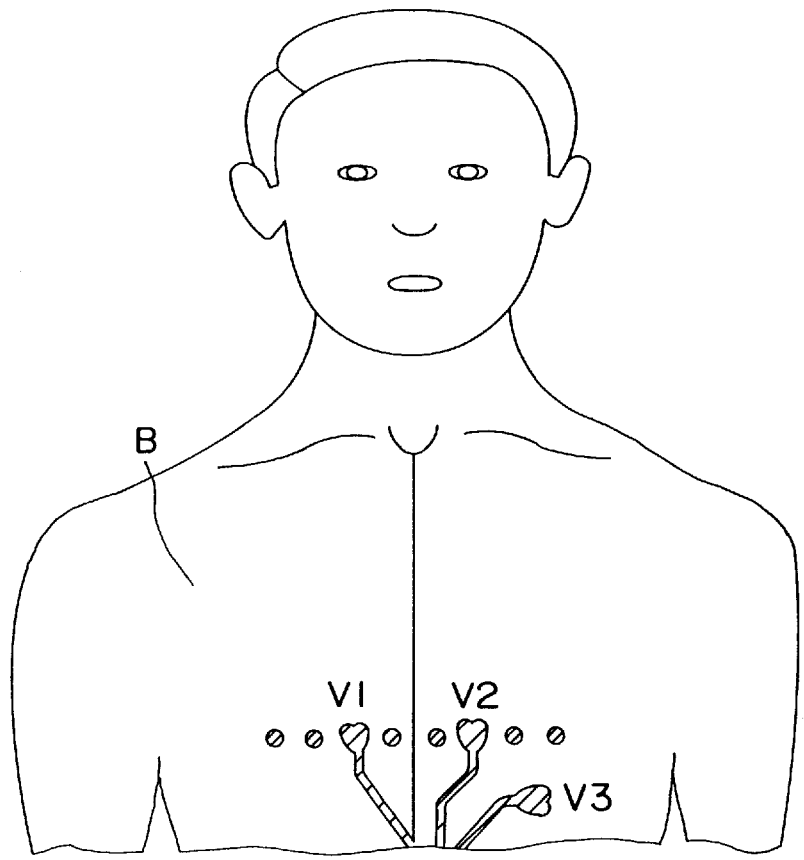
FIG. 2 shows a portion of the device illustrated in FIG. 1 as it is properly positioned on a patient.

FIG. 2 illustrates the position of the electro-dermal connector device 10 as it is properly positioned upon a patient. The connector device 10 is generally attached by adhering the precordial receptors. The receptors $V_1$ and $V_2$ are attached approximately on opposite sides of the sternum at the fourth intercostal space. Receptor pads $V_3$ and $V_4$ are attached over the ribs, with pad $V_3$ positioned approximately equidistant between $V_2$ and $V_4$. Pads $V_5$ and $V_6$ are placed at the side of the torso so that $V_5$ is substantially midway between $V_4$ and $V_6$. For small sizes the distance between $V_4$ and $V_6$ is on the average of 3.5 inches, for medium sizes 5.0 inches and for large sizes 7 inches. Of course, these measurements have a degree of tolerance, e.g., ±1.0 inch, to provide a range within which the connector device operates effectively. It should also be appreciated that distances between any of the receptor pads that fall outside the ranges disclosed herein are still considered to be within the scope of the invention as long as an effective, easy to use connector device is provided in consonance with the disclosed invention. The contour of the template 10 is configured to conform substantially to the shape of a human trunk.

In cross section a preferred laminate of the invention comprises the following layers:

a) a flexible non-conductive film of polyethylene terphthalate;

b) a catalyst layer in contact with silver ink;

c) a connector strip comprised of silver ink;

d) a dielectric layer in contact with silver ink;

e) a conductive hydrogel layer superimposed upon the silver ink layer; and f) a flexible release liner as the top layer superimposed upon the conductive hydrogel.

The flexible non-conductive web or sheet 11 may be formed from any non-conductive flexible natural or synthetic sheet material which is capable of accepting a print. Generally any cellulosic material, polyester, polyolefin, polyvinyl chloride, nylon or mixtures thereof would be suitable. Cotton, polypropylene, polyethylene can be used because of cost. However, polyester is most preferred. The polymer sheet material may be color coded for specific body areas or may contain an outline and/or color markings to simplify attaching or positioning of the electro-dermal connector device. As mentioned earlier the device of this invention is designed to include the use by an untrained or trained individual. This device allows an untrained person including the patients themselves to obtain highly reliable and repeatable ECG signals.

The receptors 22 can be made of any electrically conductive material, e.g., metals, conductive polymers, graphite, carbon fibers and the like. Conductive materials such as gold, copper, silver, tin, aluminum, N-vinyl pyrrolidone and alloys or mixtures thereof may be used. The electrode can also be made of metal foil or made from a conductive paste of a metal in particle form in a suitable binder which is printed or silk screened onto the flexible non-conductive sheet. The conductive polymer may be heat pressed or otherwise conventionally adhered to the web or sheet.

Copper strips may be electrolessly deposited on the polymeric sheets in a range of thickness from about 0.25 to about 5 microns, more preferably from 0.25 to 1.5 microns and most preferably 0.4 microns in thickness.

If desired, the exposed conductive strips may be partially coated with a dielectric polymeric material so that only selective portions are exposed. Suitable dielectric coatings include polyesters, ethylene-vinyl acetate copolymers, polyvinyl chloride and its copolymers, terpolymers such as acrylonitrile-butadiene styrene (ABS resins) and inter alia.

Preferable to copper, however, a metallic ink may be used, such as a silver ink commercially available and marketed by Dupont Chemical Corp. of Wilmington, Del. under the tradename Composition 9793.

One conductive adhesive hydrogel used is manufactured by Polyflex Circuits. Other suitable conductive adhesives are sold commercially by Lec Tec Corporation of Eden Prairie, MN and by 3M Corporation of St. Paul, Minn. Although an adhesive hydrogel is preferred any commercial electro-dermal adhesive would be operable. Preferably the area size of the hydrogel is between about 3 and 9 square centimeters.

The flexible release liner may be made from a suitable dielectric film or coated paper which includes polyesters, olefinic polymers, polyvinyl chloride and its copolymers, acrylic rubbers, ABS resin and the like.

In a preferred embodiment the electro-dermal connector 10 comprises at least six gel contact areas and is adapted for use in electrocardiography.

In accordance with the subject invention, the electro-dermal connector device 10 is available in various sizes. More specifically, by properly positioning the dimensional array $V_1$–$V_6$, a connector device having three sizes (small, medium and large) is sufficient to accommodate nearly any size adult person. In positioning the array, it has been found that the distance between pads $V_1$ to $V_4$ is generally consistent for all sizes. The dimensions between $V_1$, $V_2$, $V_3$ and $V_4$ have been developed to accommodate nearly all adults within tolerances acceptable for the resting ECG. It has also been found that body placement for pads $V_5$ and $V_6$ vary depending on individual size. Although in this embodiment three sizes are disclosed, it will be appreciated that connector devices of different sizes are well within the scope of the invention.

Figure 4:
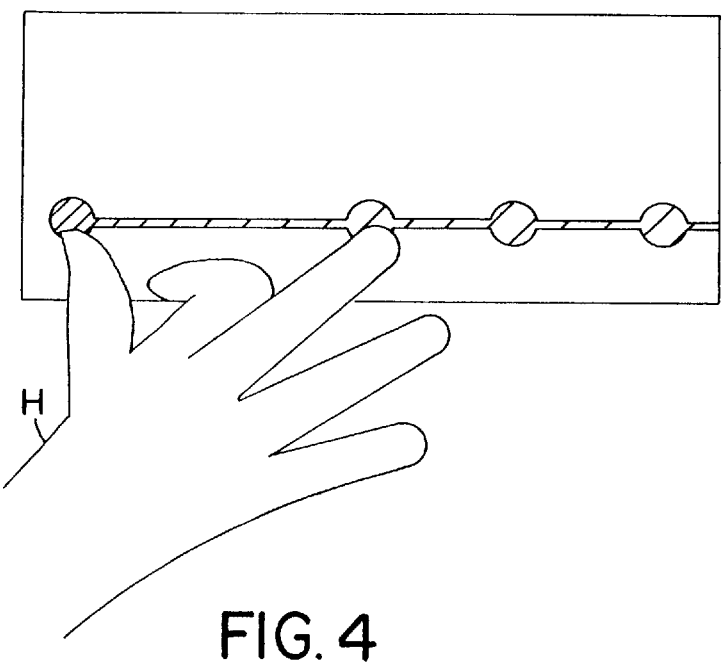
FIG. 4 shows another step in the method for determining the size of the device to be placed on a patient according to this invention.
Figure 3:
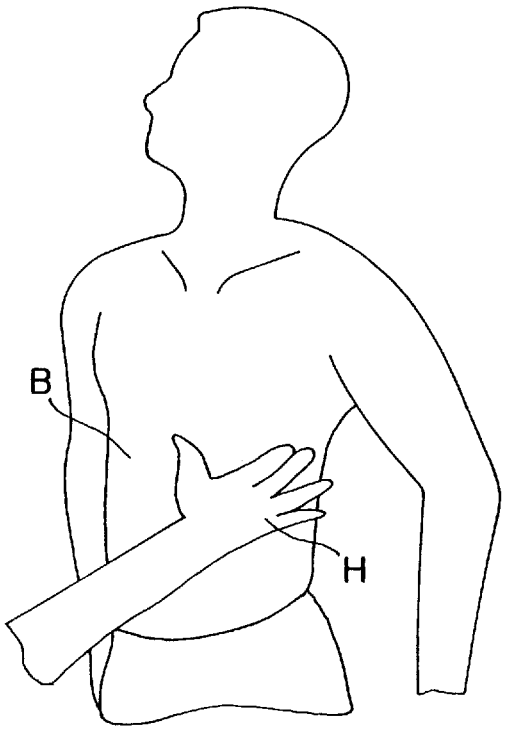
FIG. 3 illustrates the first step in the method for determining the size of the device to be used on a patient according to this invention.

FIG. 3 shows a method of determining the proper size. In this figure, the measurement M from the $V_4$ position to $V_6$ position determines the size of the device. This measurement can be determined by having the technician measure, such as by using his/her thumb and the middle finger, the distance between the midclavicular line and midaxillary line on the chest of the patient. This distance is then matched to a scale provided as shown in FIG. 4. The table below corresponds to the illustrated scale.

TABLE I

| SIZE | $V_4-V_5$ | $V_5-V_6$ |
|---|---|---|
| Small | 1.75" | 1.75" |
| Medium | 2.50" | 2.50" |
| Large | 3.50" | 3.50" |

Generally, the size of the vest is determined by the distance between $V_4$ to $V_6$. That is, the distance between the midclavicular line and the midaxillary line on the patient. For a small vest the distance between $V_4$ and $V_6$ can range from about 2.5 to 4.5 inches, for the medium vest the distance can range from about 4.0 to 6.0 inches, and for the large vest the distance can range from about 6.0 to 8.0 inches.

Figure 6:
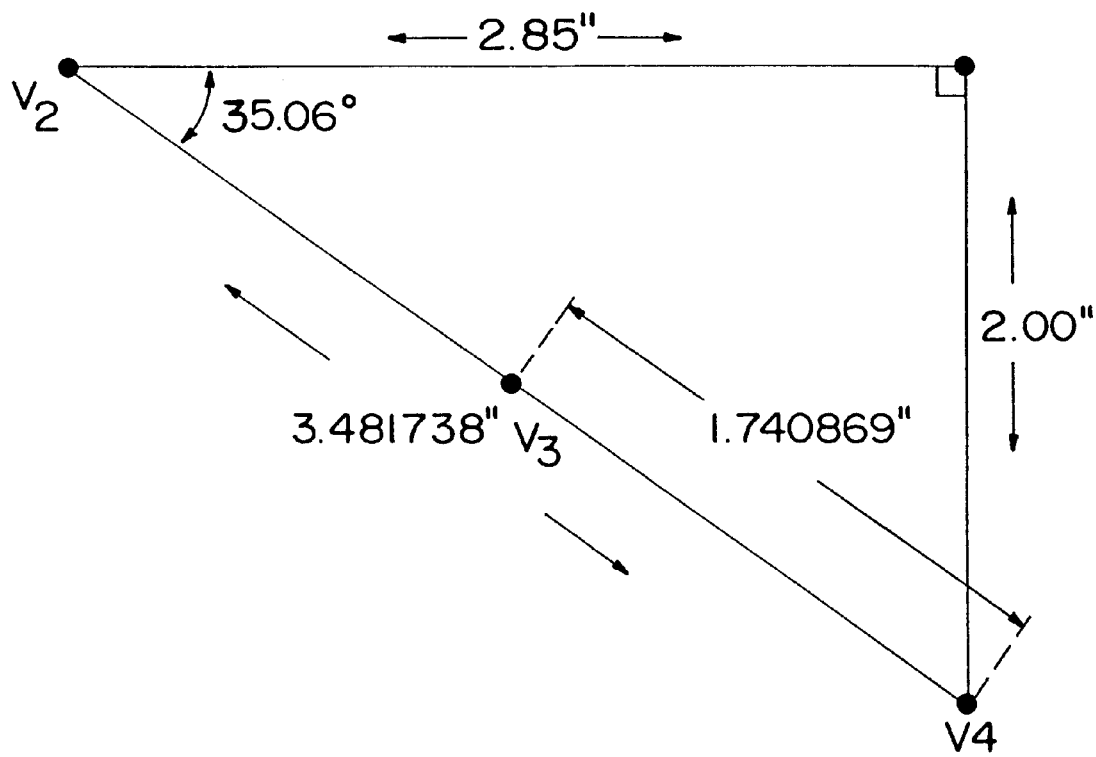
FIG. 6 shows preferred dimensions of receptors $V_2$, $V_3$ and $V_4$ in the dimensional array.

In all sizes of the device of the invention, $V_1$, $V_2$, $V_3$ and $V_4$ are generally positioned the same. With reference to FIG. 5, the center of $V_1$ is located on a point generally about 2.00 inches ±0.56 inches from the center of $V_2$ approximately on the 270 (90) degree radial from the center of $V_2$ wherein the radial is measured with zero degrees from the top of $V_2$. The center of $V_4$ is located on a point generally 3.5 inches ±1.00 inch from the center of $V_2$ approximately on the 125 (235) degree radial from the center of $V_2$. The center of $V_3$ is in line with $V_2$ and $V_4$ and is located on a point substantially between the center of $V_2$ and the center of $V_4$. FIG. 6 shows preferred dimensions for $V_2$, $V_3$ and $V_4$.

Figure 7A:
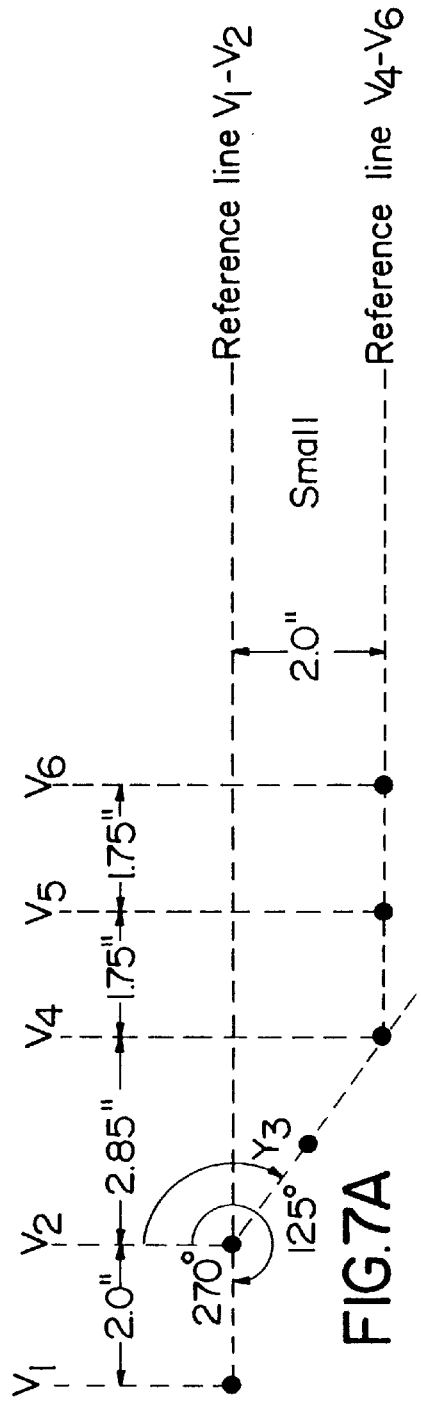
FIGS. 7A–7C show a dimensional layout of a small, medium and large device according to this invention.
Figure 7B:
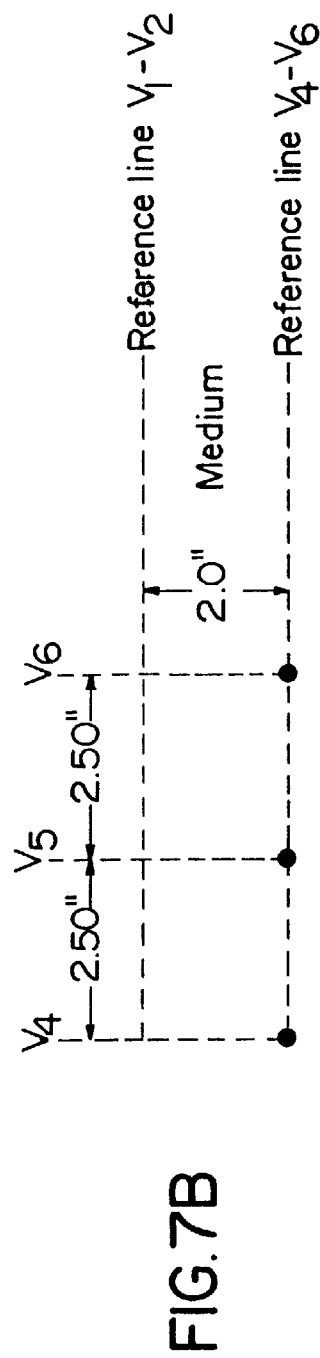
Figure 7C:
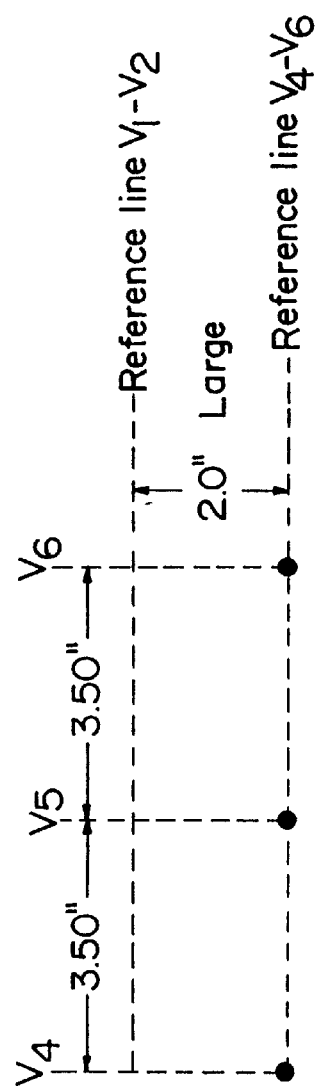

A typical dimensional layout for $V_5$ and $V_6$ relative to $V_4$ is shown in FIGS. 7A, 7B and 7C, and is as follows:

TABLE II

| SIZE | $V_4-V_5$ | $V_5-V_6$ |
|---|---|---|
| Small | 1.75" | 1.75" |
| Medium | 2.50" | 2.50" |
| Large | 3.50" | 3.50" |

The distance between $V_1$ and $V_2$ is 2.00 inches, the distance between sternum centerline and $V_4$ along a horizontal line is 3.85 inches and the distance between $V_2$ and $V_4$ along a vertical line is 2.00 inches, although this vertical distance could be up to 3.50 inches without considerably altering the effectiveness of the device. In addition, $V_3$ is located on a diagonal line between $V_2$ and $V_4$ and is equidistant from $V_2$ and $V_4$.

As discussed above, the connector device can be sized to accommodate practically any size adult person. Even if the person is smaller than the "small" size device, a connector device of the small (or even medium or large) size can be used by folding the flexible sheet 11 over on itself to reduce the distances between the connector arrays as appropriate.

Although a specific embodiment of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A disposable electrodeless electro-dermal connector device comprising:

a flexible non-conductive sheet comprising a fixed array of electrical conductor strips affixed thereon and positioned in a specific size configuration appropriate for electrocardiographic recording, said conductor strips having receptor ends $V_1$ to $V_6$ adapted for electrical connection with the skin for receiving and transmitting electrical impulses and a terminal connection end which is adapted for connection with an electrocardiological measuring apparatus, with said receptor ends $V_1$, $V_2$, $V_3$ and $V_4$ positioned at predetermined fixed locations on said sheet and said receptor ends $V_5$ and $V_6$ positioned at predetermined fixed locations on said sheet which vary dependent on patient size.

2. The connector device of claim 1, wherein the distance between $V_1$ and $V_2$ is 2.00 inches ±0.56 inches and the distance between $V_2$ and $V_4$ is 3.5 inches ±1.00 inch, with $V_3$ located substantially midway between $V_2$ and $V_4$, and $V_5$ is equidistant between $V_4$ and $V_6$.

3. The connector device of claim 1, wherein said non-conductive sheet is selected from non-conductive flexible natural or synthetic sheet material.

4. The connector device of claim 3, wherein said non-conductive sheet is selected from cellulosic materials, polyesters, polyolefins, polyvinyl chloride or nylon.

5. The connector device of claim 4, wherein said cellulosic material is cotton or paper.

6. The connector device of claim 4, wherein said polyester is polyethylene terphthalate.

7. The connector device of claim 1, wherein the conductor strips are selected from metal, polymer, graphite or carbon fibers.

8. The connector device of claim 7, wherein said metal is selected from gold, copper, silver, tin or aluminum and alloys or mixtures thereof.

9. The connector device of claim 8, wherein said conductor strips are made of metal foil or a metal paste.

10. The connector device of claim 9, wherein said paste is printed or silk screened onto said non-conductive sheet.

11. The connector device of claim 10, wherein said paste is electrolessly deposited on said non-conductive sheet.

12. The connector device of claim 8, wherein said conductor strips are less than 10 microns in thickness.

13. The connector device of claim 7, wherein the conductive strips are coated with a dielectric polymeric material so that only sensitive portions are exposed.

14. The connector device of claim 13, wherein said polymeric material is selected from the group consisting of polyesters, copolymer of ethylene-vinyl acetate, homopolymers and copolymers of polyvinylchloride and ABS resin.

15. The connector device of claim 1, wherein the distance between $V_4$ and $V_5$ and between $V_5$ and $V_6$ is about 1.75 inches.

16. The connector device of claim 1, wherein the distance between $V_4$ and $V_5$ and between $V_5$ and $V_6$ is about 2.5 inches.

17. The connector device of claim 1, wherein the distance between $V_4$ and $V_5$ and between $V_5$ and $V_6$ is about 3.5 inches.

18. The connector device of claim 1, wherein $V_1$ is located 2.00 inches ±0.56 inches in radius on about a 270 degree radial from the center of $V_2$.

19. The connector device of claim 1, wherein $V_3$ is located on about a 125 degree radial from the center of $V_2$.

20. A method of fitting a patient with an electrodeless electro-dermal connector device comprising a flexible non-conductive sheet comprised of a fixed array of electrical conductor strips affixed thereon and positioned in a specific size configuration appropriate for electrocardiographic recording, the conductor strips having receptor ends $V_1$ to $V_6$ adapted for electrical connection with the skin for receiving and transmitting electrical impulses and a terminal connection end which is adapted for connection with an electrocardiological measuring apparatus, with said receptor ends $V_1$, $V_2$, $V_3$ and $V_4$ positioned at predetermined fixed locations on said sheet and said receptor ends $V_5$ and $V_6$ positioned at predetermined fixed locations on said sheet dependent on patient size, said method comprising the steps of:

measuring the distance between a midclavicular line and a midaxillary line on the chest of the patient;

selecting a connector device with receptor ends $V_5$ and $V_6$ positioned at their predetermined fixed locations based on the measured distance; and positioning the selected connector device on the patient.

21. A method of fitting a patient according to claim 20, further comprising the step of selecting a connector device with a distance of 1.75" between $V_4$ and $V_5$ and 1.75" between $V_5$ and $V_6$ when the measured distance is between 2.5" and 4.5".

22. A method of fitting a patient according to claim 20, further comprising the step of selecting a connector device with a distance of 2.5" between $V_4$ and $V_5$ and 2.5" between $V_5$ and $V_6$ when the measured distance is between 4.0" and 6.0".

23. A method of fitting a patient according to claim 20, further comprising the step of selecting a connector device with a distance of 3.5" between $V_4$ and $V_5$ and 3.5" between $V_5$ and $V_6$ when the measured distance is between 6.0 and 8.0".

24. A method of fitting a patient according to claim 20, wherein the distance between $V_1$ and $V_2$ is 2.00 inches ±0.56 inches, and the distance between $V_2$ and $V_4$ is 3.5 inches ±1.00 inch, with $V_3$ located substantially midway between $V_2$ and $V_4$, and $V_5$ is equidistant between $V_4$ and $V_6$.

25. A process of forming an electrodeless electro-dermal connector device, comprising the steps of:

providing a flexible sheet for supporting a fixed array of electrical conductor strips;

affixing an array of electrical conductor strips on the flexible sheet in a specific size configuration appropriate for electrocardiographic recording, with the conductor strips having receptor ends $V_1$–$V_6$ adapted for electrical connection with the skin for receiving and transmitting electrical impulses and a terminal connection end which is adapted for connection with an electrocardiological measuring apparatus;

positioning the electrical conductor strips so that receptor ends $V_1$, $V_2$, $V_3$ and $V_4$ are disposed at predetermined fixed locations on the sheet; and positioning the electrical conductor strips so that receptor ends $V_5$ and $V_6$ are disposed at predetermined fixed locations on the sheet which vary dependent on patient size.

26. A process according to claim 25, further comprising the step of positioning the receptor ends $V_1$–$V_6$ such that the distance between $V_1$ and $V_2$ is 2.00 inches ±0.56 inches, and the distance between $V_2$ and $V_4$ is 3.5 inches ±1.00 inch, with $V_3$ located substantially midway between $V_2$ and $V_4$, and $V_5$ is equidistant between $V_4$ and $V_6$.

27. A process according to claim 25, further comprising the step of positioning receptor ends $V_5$ and $V_6$ based on a measured distance between a midclavicular line and a midaxillary line on the chest of the patient.

28. A process according to claim 25, further comprising the step of positioning receptor ends $V_1$ and $V_2$ to be approximately on either side of the sternum at the fourth intercostal space and positioning receptor end $V_3$ to be approximately midway between $V_2$ and $V_4$.

29. A process according to claim 25, wherein the distance between $V_4$ and $V_5$ and between $V_5$ and $V_6$ for a small size is about 1.75 inches, for a medium size is about 2.5 inches, and for a large size is about 3.5 inches.

30. A process according to claim 25, wherein $V_1$ is located 2.00 inches ±0.56 inches in radius on about a 270 degree radial from the center of $V_2$.

31. A process according to claim 25, wherein $V_3$ is located on about a 125 degree radial from the center of $V_2$.

32. A plurality of electro-dermal connector devices of different sizes, with each device comprising:

a flexible non-conductive sheet comprising a fixed array of electrical conductor strips affixed thereon and positioned in a specific size configuration appropriate for electrocardiographic recording, said conductor strips having receptor ends $V_1$ to $V_6$ adapted for electrical connection with the skin for receiving and transmitting electrical impulses and a terminal connection end which is adapted for connection with an electrocardiological measuring apparatus, with the receptor ends $V_1$, $V_2$, $V_3$ and $V_4$ positioned at predetermined fixed locations on each said size, and receptor ends $V_5$ and $V_6$ positioned at predetermined fixed locations on each said size which vary dependent upon the size of the patient.

33. A plurality of electrodermal connector devices as set forth in claim 32, wherein on each device the distance between $V_1$ and $V_2$ is 2.00 inches ±0.56 inches, and the distance between $V_2$ and $V_4$ is 3.5 inches ±1.00 inch, with $V_3$ located substantially midway between $V_2$ and $V_4$, and $V_5$ being generally equidistant between $V_4$ and $V_6$.

* * * * *